United States Patent [19]

Cutruzzula et al.

[11] 4,059,105
[45] Nov. 22, 1977

[54] CANNULA SECURING DEVICE

[75] Inventors: Jeffrey F. Cutruzzula, Pittsburgh, Pa.; Robert L. Schattner, Baltimore, Md.

[73] Assignee: Omnimed, Inc., Burlington, N.J.

[21] Appl. No.: 669,782

[22] Filed: Mar. 24, 1976

[51] Int. Cl.² ............................................. A61M 5/00
[52] U.S. Cl. .......................... 128/133; 128/DIG. 26; 128/214 R
[58] Field of Search .................. 128/214 R, 133, 215, 128/221, 348–351, DIG. 26; 24/DIG. 11; 248/205 A

[56] References Cited

U.S. PATENT DOCUMENTS

| 3,001,735 | 9/1961 | Francik | 24/DIG. 11 |
| 3,046,984 | 7/1962 | Eby | 128/DIG. 26 |
| 3,430,300 | 3/1969 | Doan | 128/349 R X |
| 3,885,560 | 5/1975 | Baldwin | 128/214 R |
| 3,918,446 | 11/1975 | Buttaravoli | 128/133 |
| 3,973,565 | 8/1976 | Steer | 128/214.4 |

Primary Examiner—Dalton L. Truluck
Attorney, Agent, or Firm—Leitner, Palan & Martin

[57] ABSTRACT

A lamina having a wide head portion foldable about a lateral weakening to be superimposed on a narrow body portion which includes an elongated opening. Adhesive on the wide head portion and the narrow body portion secure the lamina to a common surface.

16 Claims, 4 Drawing Figures

CANNULA SECURING DEVICE

BACKGROUND OF THE INVENTION

1. Field of the Invention

The present invention relates generally to a securing device and more specifically to an adhesive lamina used to secure a cannula to the patient in whom the cannula is inserted.

2. Description of the Prior Art

In the field of medicine, a needle or catheter or cannula which is inserted intravenously into a patient is usually secured to the patient by taping. This generally includes the positioning of a gauze pad and the tearing and applying of a plurality of strips of tape to secure the cannula and associated tubing to the patient to prevent the accidental removal of the cannula from the patient by sudden movement. Not only is the tearing of adhesive strips time consuming, but the number of strips and the degree of protection, for accidental removing of the cannula by sudden movement, is purely the function of the knowledge and training of the technician, nurse or other medical person involved. Also the ease of viewing the site at which the cannula is inserted is dependent upon the pattern of which the attendent applies the strips of tape as well as the size of the gauze pad used. By obscuring the insertion site, infiltration is undetected.

A securement device directed to this problem is shown by Buttaravoli in U.S. Pat. No. 3,918,446, which also lists pertinent patents of the prior art. Buttaravoli's device deals with a sandwich concept for the catheter and associated tubing. The bottom most layer must be slid around and underneath the inserted catheter. This operation is very delicate and requires movement of the catheter which is not only uncomfortable to the patient, but could also cause infiltration and other injuries at the insertion site. The sandwich concept increases the cost of the device and the amount of time used to apply the device is not an improvement over prior art devices. Also, Butaravoli's device obscures a significant portion of the area surrounding the insertion site.

Thus there exists a need for a standard, economical, easy to apply device for securing a cannula to a patient in which it is inserted, which facilitates a standard of applying, minimizes the obscured area, and allows ease of inspection of the site of insertion.

SUMMARY OF THE INVENTION

The present invention is a cannula securing device which overcomes the problems of the prior art by providing a unitary lamine having a narrow portion including an elongated opening to surround and expose the site at which the cannula enters the patient and a wide portion which, when superimposed upon the narrow portion by folding, covers the opening and a portion of the tubing connected to the cannula and lying adjacent and essentially parallel to length of the narrow portion. The narrow portion includes an adhesive on a surface to secure the distal portion of the cannula to the patient and the wide portion has an adhesive on a surface for securing the portion of tubing laying adjacent the narrow portion to the patient as well as the exposed portion of the cannula. The narrow portion includes a pair of ears extending from the base thereof to increase the adhesive quality of the narrow portion to the patient. The narrow portion is weakened along its width to facilitate the folding of the wide portion upon the narrow portion. The wide portion is of a sufficient length so as to cover the elongated opening as well as the ears of the narrow portion when superimposed thereon. A substantial area of the surface opposite the adhesive surface of the narrow portion is treated to prevent the superimposed wide portion from adhering thereto to facilitate inspection of the insertion site. An adhesive on the remaining area of the treated surface coacts with the adhesive on a corresponding area of the wide portion when superimposed to limit the angle of unfolding for viewing the site.

OBJECTS OF THE INVENTION

An object of the present invention is to provide an economical, easy to apply device for securing a cannula to a patient in whom it is inserted.

Another object is to provide a device for securing a cannual to a patient in whom it is inserted which allows for ease of inspection of the insertion site.

A further object of the invention is to provide a device for securing a cannula to the patient in whom it is inserted which protects the cannula from accidental removal by sudden movement.

An even further object is to provide a securing device which maximises the viewable area of the patient by minimizing the area of the lower portion of the device.

Other objects, advantages and novel features of the present invention will become apparent from the following detailed description of the invention when considered in conjunction with the accompanying drawings.

DESCRIPTION OF THE PREFERRED EMBODIMENTS

Figure 1:
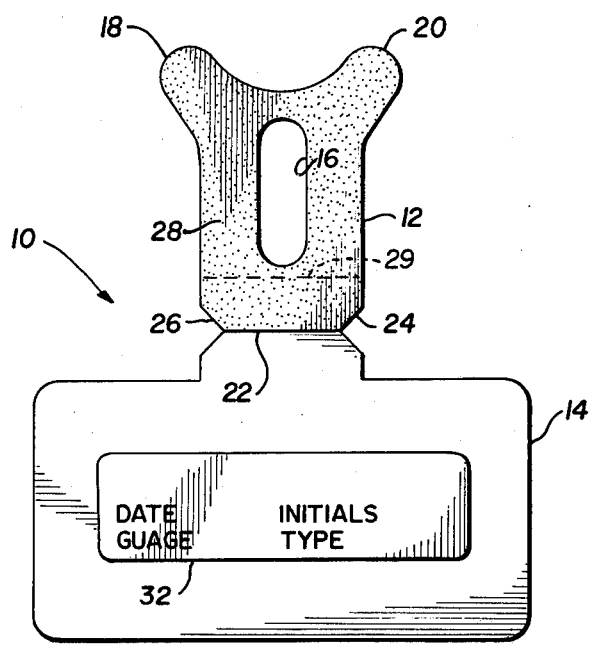
FIG. 1 is a plan view of a preferred embodiment of the cannula securing device of the present invention.

FIG. 1 illustrates a preferred embodiment of the cannula securing device 10 having a narrow portion 12 and a wide portion 14. The securing device may be considered generally a T-shaped lamina wherein portion 12 is the body portion and portion 14 is the head portion. The narrow body portion 12 has an elongated opening 16 therein and a pair of ears or protuberances 18 and 20 extending from the base thereof. The narrow body portion 12 has a weakened portion 22 therein to facilitate the folding of the wide head portion 14 so as to be superimposed upon the narrow body portion 12. A pair of notches 24 and 26 may also be provided to facilitate the folding.

An adhesive 28 is applied on a first surface of the narrow body portion 12, which is the top surface viewed in FIG. 1. An adhesive 30 is also applied to the wide head portion 14 on a surface, opposite the first surface, which is the bottom surface as viewed in FIG. 1, and the top surface in FIG. 2. The adhesive 30 applied to portion 14 also extends on to a part of the narrow body portion 12 and terminates at the dotted line illustrated in FIG. 1 as 29. As will be explained below, the adhesive area 31 between the line 29 and the weakened portion on 22 coacts with the adhesive area 33 when superimposed to adhere thereto and limit the angle of the wide head portion when lifted or unfolded.

The adhesive applied to the surfaces of the lamina are covered by an appropriate material (not shown), for example, paper, to prevent the drying out or accidental adhesion of the lamina until used.

A label 32 is provided upon the nonadhesive surface of the wide head protion 14 on which appropriate indicia, for example, the date of insertion, the gauge of the cannula, the initials of the attendant, and the type of liquids being provided to or drawn by the cannula may be recorded.

The lamina may be made of foamed copolymer, for example, polystyrene, cloth, or any other appropriate material which is sufficiently flexible to allow bending and cushioning. The weakening of the narrow body portion may be produced by scoring, perforating, embossing or other known methods. The adhesive is a surgical grade of adhesive which is sterilizable and is not so aggressive as to deteriorate the skin.

Figure 2:
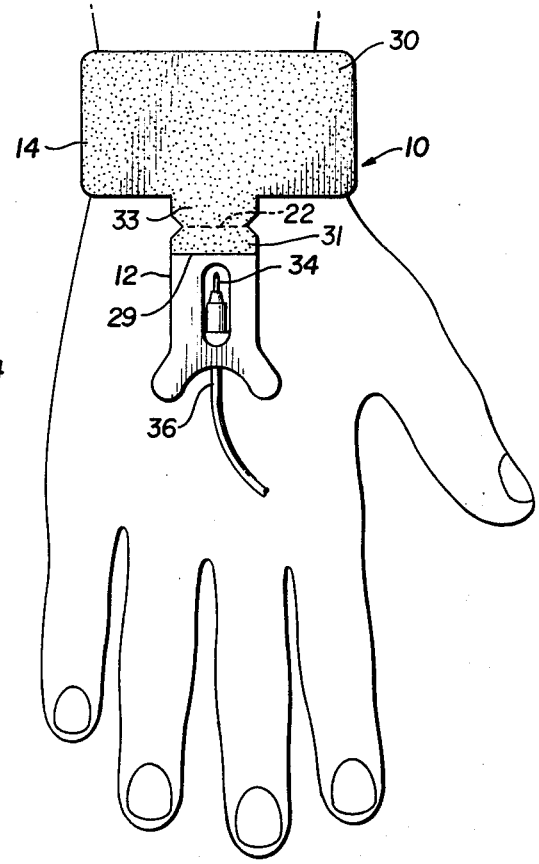
FIGS. 2 through 4 depict the sequential operation of applying the preferred embodiment of the cannula securing device of the present invention to the patient in whom the cannula is inserted.
Figure 3:
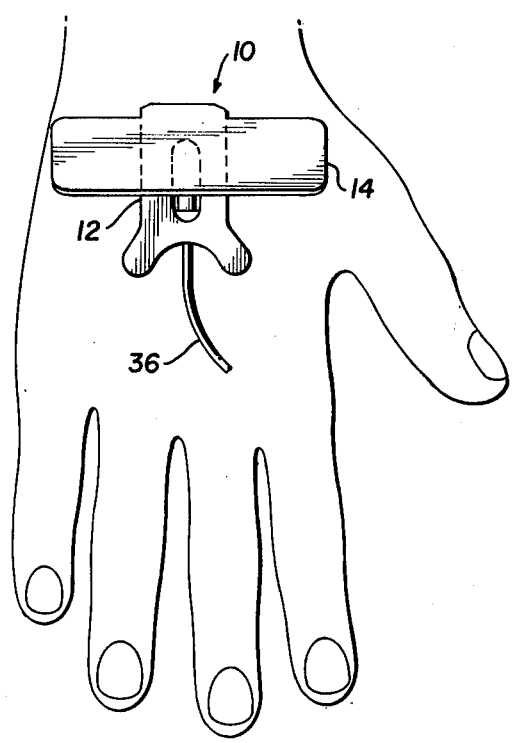
Figure 4:
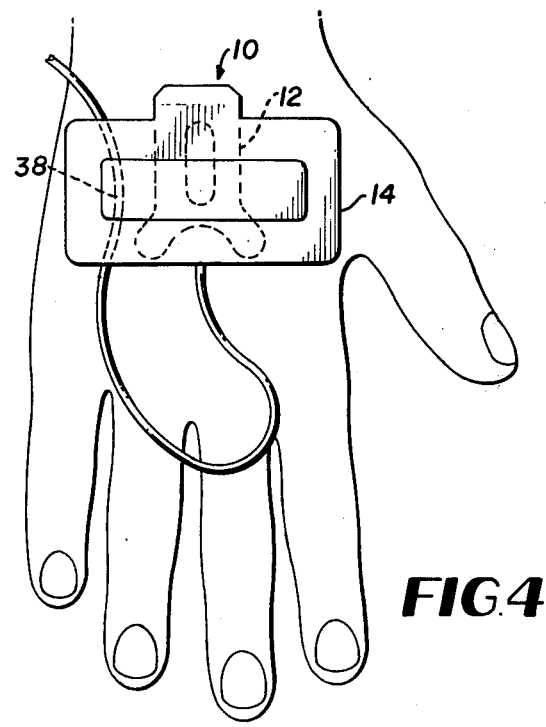

The method of use of the cannula securing device of the present invention is illustrated in FIGS. 2 through 4. The site of insertion is prepared by cleaning and the needle, catheter, or cannula is inserted. A protective sheet of paper (not shown) is removed from the narrow body portion 12 of the cannula securing device 10. The elongated opening 16 is positioned over the site of the insertion to expose the insertion site and the cannula 34. The adhesive side of the narrow body portion 12 is then applied to the patient around the insertion site while positioning a portion 36 of the tubing associated with and connected to the cannula between the pair of ears 18 and 20. The length and width of the narrow portion 12 is maintained at a minimum to maximize the unobstructed area of the insertion site, while providing sufficient contact area for adequate adhesion to the patient including the distal portion of the cannula.

Next a protective sheet of paper (not shown) is peeled from the adhesive side of the wide head portion 14 of the cannula securing device. A second portion 38 of the tubing is placed adjacent and substantially parallel to the narrow body portion 12 of the cannula securing device. The wide head portion 14 is then folded about the weakened area 22 to be superimposed upon the narrow body portion 12 and the tube portion 38 and to secure them to the patient. While the narrow body portion 12 secures the distal end of the cannula to the patient, the wide head portion 14 secures the remainder of the cannula as well as the portion 38 of the tubing to the patient.

It should be noted that the length of the wide head portion 14 is selected so as to completely cover the elongated opening 16 as well as the end of ears 18 and 20 of the narrow body portion 12. As viewed in FIG. 3, the cannula securing device of the present invention completely hides the site of insertion from view of the patient as well as protects the cannula from accidental removal caused by sudden movement.

When the insertion site is to be viewed for filtrations or other abnormalities, the wide head portion 14 is raised. Since superimposed areas 31 and 33 have adhesive and do not separate, the wide head portion 14 essentially bends about a line substantially coincident with line 29. The thickness of the lamina in combination with the double adhesive limits the angle of unfolding of the wide head portion to essentially ninety degrees thereby minimizing the obstructed area and the probability of dislocating the lower narrow body portion 12.

Depending upon the material selected for the lamina, it may be advantageous to treat the second surface, opposite the first surface, of the narrow body portion 12 with a coating, for example, petroleum jelly, such that the adhesive on the wide head portion 14 will not stick thereto. This is important because when the wide head portion 14 is raised to view the site, the interaction between the surfaces may cause the narrow body portion 12 to also be removed and thus unsecure and possibly pull the cannula from the patient. By applying the cannula securing device 10 from above, the probability of moving the inserted cannula is reduced and the cannula is secured to the patient and protected by two superimposed adhesive cushioning layers.

From the proceeding description of the preferred embodiments, it is evident that objects of the invention are attained and although the invention has been described and illustrated in detail, it is to be clearly understood the same is by way of illustration and example only and is not to be taken by way of limitation. The materials selected for the lamina as well as the adhesive mentioned are mere examples. Although the narrow body portion 12 and the wide head portion 14 are illustrated as rectangular and of constant width, the securing device will function as well if the narrow and wide portions are of irregular shapes as long as a narrow portion minimizes the obstructed area and a wide portion exceeds the width of the narrow portion. The spirit and scope of this invention being limited only by the terms of the appended claims.

What is claimed:

1. A securing device comprising a generally T-shaped lamina having a head and a body portion, said body portion having an opening means confined therein for permitting viewing of a portion of the skin of a subject surrounded by said body portion, said body portion also having adhesive on a first surface to adhere to said subject and said head portion having adhesive on a second surface opposite said first surface and being sufficiently wider than said body portion on both sides to adhere to said subject when superimposed on said body portion.

2. The securing device of claim 1 wherein said body portion includes a pair of ears projecting from the base end of said body portion.

3. The securing device of claim 1 wherein said opening means is an elongated opening extending along the length of said body portion and constituting a substantial portion of said body portion.

4. The securing device of claim 1 wherein said lamina is a single piece of material.

5. The securing device of claim 3 wherein the length of said head portion is greater than the length of said elongated opening.

6. The securing device of claim 5 wherein said lamina is weakened along the lateral axis so that said head portion covers said opening and the base of said body portion when superimposed thereon by folding.

7. A method for securing a cannula and associated tubing to a subject in which the cannula is inserted comprising:
positioning an elongated opening of a narrow portion of a lamina over the site of said insertion to expose a portion of said cannula at said insertion;
applying an adhesive surface of said narrow portion to the subject around said site and over a portion of said cannula to secure said cannula to said subject;
folding a wide portion of said lamina over a top of said narrow portion; and applying an adhesive surface of said wide portion to said subject and said narrow portion.

8. The method of claim 7 wherein positioning an elongated opening includes positioning a portion of said tubing adjacent said cannula between a pair of ears extending from an end of said narrow portion.

9. The method of claim 7 including the step of positioning a portion of said tubing adjacent said narrow portion along its length and wherein said adhesive surface of said wide portion is also applied to said portion of said tubing adjacent said narrow portion.

10. A cannula securing device comprising:
a lamina having a narrow portion and a wide portion;
said narrow portion having an elongated opening for surrounding and exposing the site at which said cannula is inserted into a patient and adhesive on a first surface of said narrow portion for securing said narrow portion and the distal end of said cannula to said patient; and
said wide portion having adhesive on a second surface, opposite said first surface, and being of sufficient length to cover said elongated opening and sufficient width to engage the skin of said patient on both sides when said wide portion is superimposed on said narrow portion by folding.

11. The cannula securing device of claim 10 wherein said narrow portion is weakened along its width for facilitating said folding.

12. The cannula securing device of claim 10 wherein the length of said wide portion is sufficient to cover said opening in and the base edge of said narrow portion when superimposed thereon by folding.

13. The cannula securing device of claim 10 wherein said narrow portion includes a pair of ears extending from the end of said narrow portion.

14. The cannula securing device of claim 10 wherein said lamina is a single piece of resilient material to provide a cushioning protective layer.

15. The cannula securing device of claim 10 wherein a substantial portion of a third surface of said narrow portion directly opposite said first surface is treated to prevent adhesion of said wide portion thereto.

16. The cannula securing device of claim 11 wherein an area of said second surface of said narrow portion between said weakening and said opening has an adhesive which coacts with the adhesive on a corresponding area of said wide portion when superimposed to limit the angle of unfolding.

* * * * *